US009089809B2

(12) United States Patent
Giurgiutiu et al.

(10) Patent No.: US 9,089,809 B2
(45) Date of Patent: Jul. 28, 2015

(54) METHODS AND SENSORS FOR THE DETECTION OF ACTIVE CARBON FILTERS DEGRADATION WITH EMIS-ECIS PWAS

(71) Applicants: Victor Giurgiutiu, Columbia, SC (US); Jingjing Bao, West Columbia, SC (US); Gregory William Peterson, Belcamp, MD (US)

(72) Inventors: Victor Giurgiutiu, Columbia, SC (US); Jingjing Bao, West Columbia, SC (US); Gregory William Peterson, Belcamp, MD (US); Glenn Rubel, Baldwin, MD (US)

(73) Assignee: University of South Carolina, Columbia, SC (US)

( * ) Notice: Subject to any disclaimer, the term of this patent is extended or adjusted under 35 U.S.C. 154(b) by 0 days.

(21) Appl. No.: 14/466,362

(22) Filed: Aug. 22, 2014

(65) Prior Publication Data
US 2015/0168325 A1 Jun. 18, 2015

Related U.S. Application Data

(60) Division of application No. 13/549,955, filed on Jul. 16, 2012, now Pat. No. 8,814,996, which is a continuation of application No. 13/309,149, filed on Dec. 1, 2011, now abandoned.

(51) Int. Cl.
*B01D 53/02* (2006.01)

(52) U.S. Cl.
CPC ........ *B01D 53/02* (2013.01); *B01D 2259/4583* (2013.01)

(58) Field of Classification Search
CPC ................ B01D 2253/102; B01D 2259/4583; B01D 53/02; B01D 53/0415; B01D 53/0454; F01N 9/00; G01N 29/09; G01N 29/2437
See application file for complete search history.

(56) References Cited

U.S. PATENT DOCUMENTS

| | | |
|---|---|---|
| 5,850,166 A | 12/1998 | Katoh et al. |
| 6,225,877 B1 | 5/2001 | Ozeki et al. |
| 6,375,725 B1 | 4/2002 | Bernard et al. |
| 6,540,814 B2 | 4/2003 | Hayes et al. |
| 6,996,480 B2 | 2/2006 | Giurgiutiu et al. |
| 7,024,315 B2 | 4/2006 | Giurgiutiu et al. |
| 7,174,255 B2 | 2/2007 | Giurgiutiu et al. |
| 7,875,100 B2 | 1/2011 | Wright |

(Continued)

OTHER PUBLICATIONS

Giurgiutiu, V, "Structural Health Monitoring with Piezoelectric Wafer Active Sensors", Elsevier Academic Press 2008, ISBN 978-0120887606, 760 pages.

(Continued)

*Primary Examiner* — Christopher P Jones
(74) *Attorney, Agent, or Firm* — Dority & Manning, P.A.

(57) ABSTRACT

Active carbon filters and systems that are operative to detect active carbon filter degradations are provided. The active carbon filter can include a carbon filter comprising activated carbon and defining a filter surface; a first piezoelectric wafer active sensor on the filter surface that is electrically isolated from the carbon filter; and a second piezoelectric wafer active sensor on the filter surface that is electrically connected to the filter surface; and an impedance monitoring device electrically connected to the first piezoelectric wafer active sensor and the second piezoelectric wafer active sensor. Methods are also disclosed for determining if any degradation has occurred in an active carbon filter.

6 Claims, 22 Drawing Sheets

(56) References Cited

U.S. PATENT DOCUMENTS

| | | | |
|---|---|---|---|
| 7,881,881 B2 | 2/2011 | Giurgiutiu et al. | |
| 2008/0288184 A1 | 11/2008 | Giurgiutiu et al. | |
| 2009/0048789 A1 | 2/2009 | Yu et al. | |
| 2009/0056536 A1* | 3/2009 | Wright | 95/25 |
| 2009/0188319 A1 | 7/2009 | Giurgiutiu et al. | |
| 2010/0132469 A1 | 6/2010 | Giurgiutiu et al. | |

OTHER PUBLICATIONS

Xu et al., "Development of DSP-based Electromechanical (E/M) Impedance Analyzer for Active Structural Health Monitoring", SPIE's 13$^{th}$ International Symposium on Smart Structures and Materials and 11$^{th}$ International Symposium on NDE for Health Monitoring and Diagnostics, Health Monitoring and Smart NDE of Structural and Biological Systems Conference, Feb. 26-Mar. 2, 2006, paper # 6174-26, 11 pages.

Giurgiutiu et al., "Electromechanical Impedance Sensor for In Vivo Monitoring the Body Reaction to Implants", Journal of Investigative Surgery 2004, 17, pp. 257-270.

Rubel et al., "Measurement of the impedance change of impregnated activated carbon during exposure to $SO_2$ vapors at ambient temperatures", Carbon 47 2009, pp. 3566-3573.

Hori et al, "Development of a new respirator for organic vapors with a breakthrough detector using a semiconductor gas sensor", Applied Occupational and Environmental Hygiene, 18, pp. 90-95, 2003.

Fazzino et al., "Impedance spectroscopy for progressive damage analysis in woven composites", Composites Science and Technology 2009, 69, pp. 2008-2014.

* cited by examiner

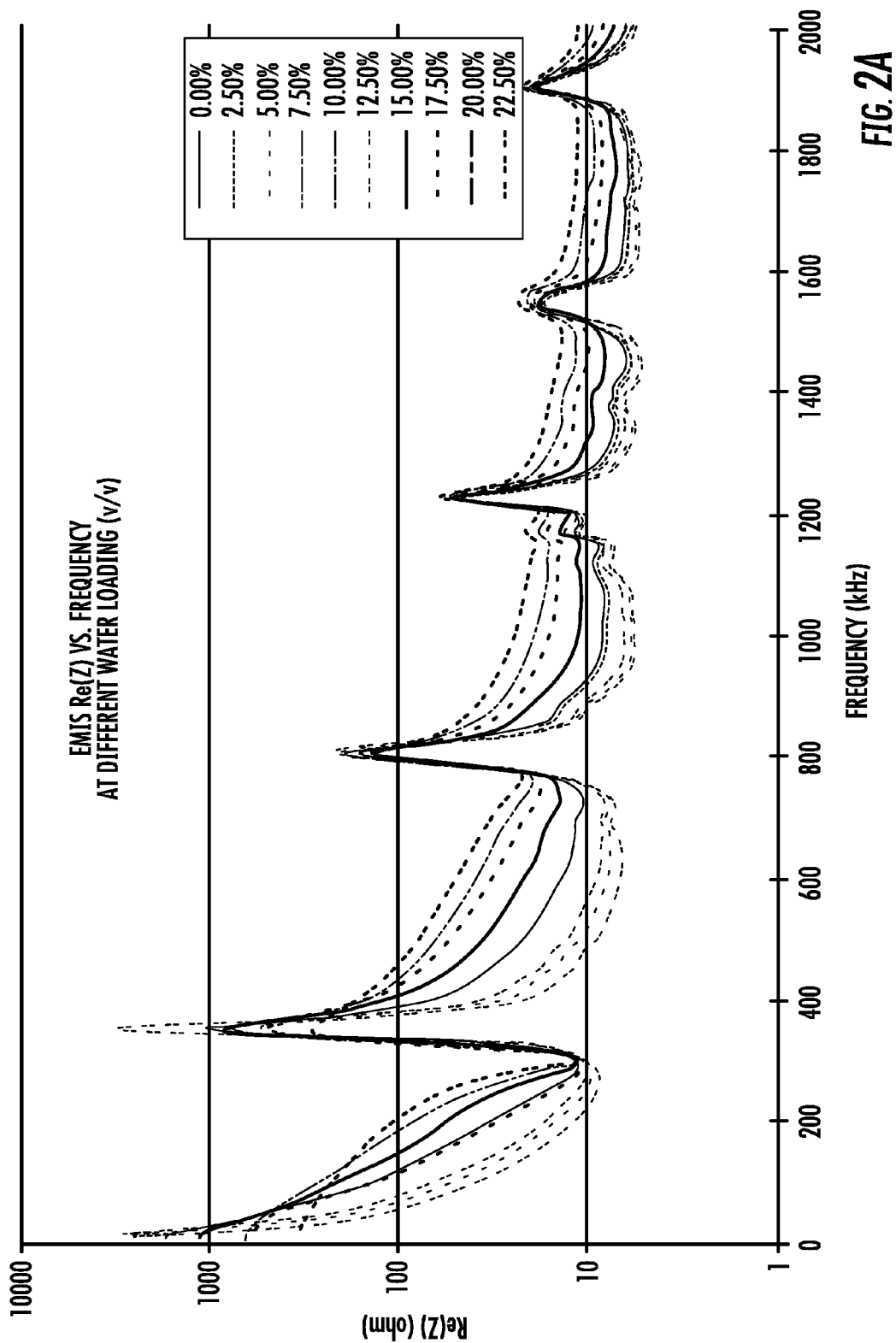

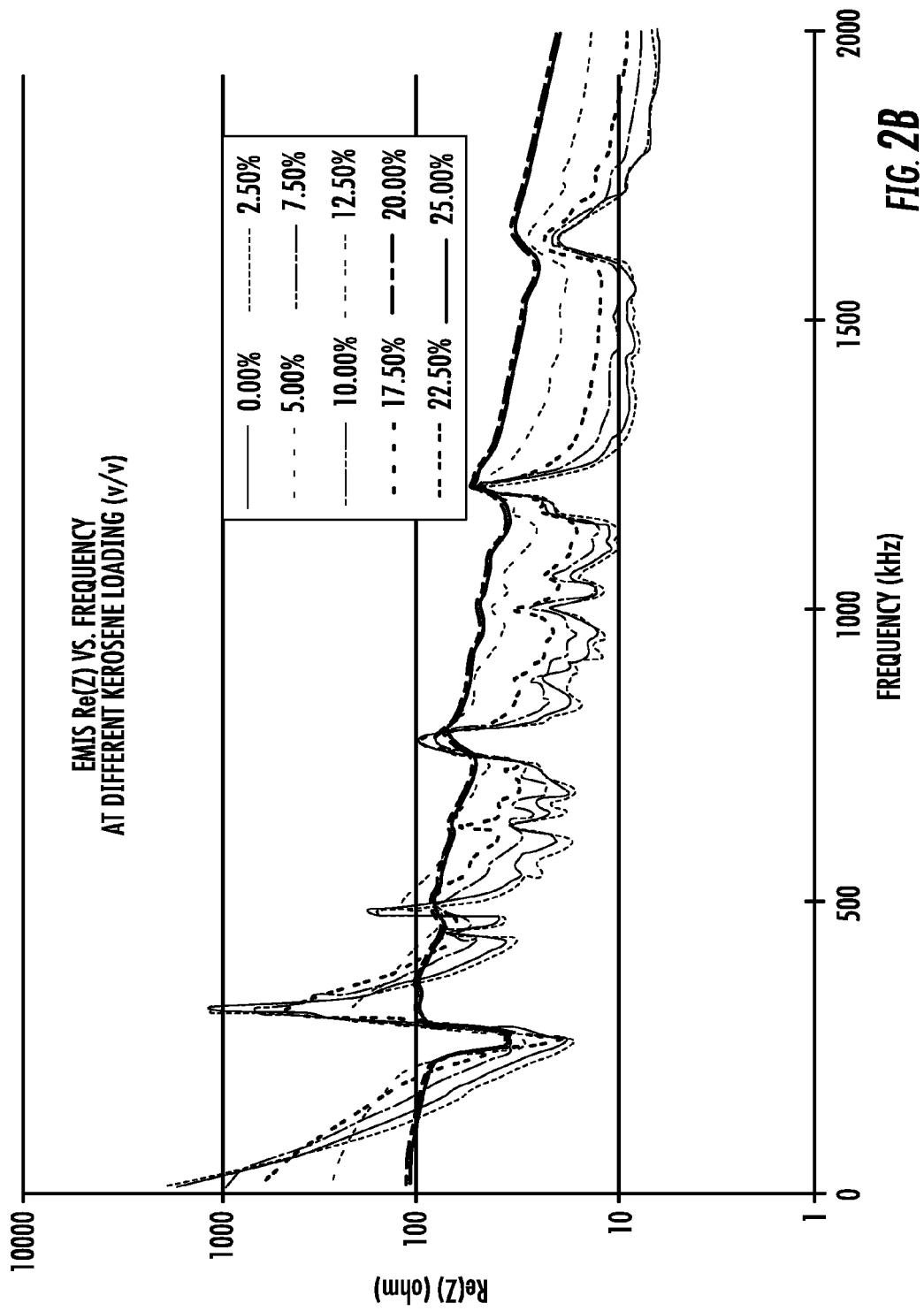

METHODS AND SENSORS FOR THE DETECTION OF ACTIVE CARBON FILTERS DEGRADATION WITH EMIS-ECIS PWAS

PRIORITY INFORMATION

The present application (1) is a divisional of and claims priority to U.S. patent application Ser. No. 13/549,955 titled "Methods and Sensors for the Detection of Active Carbon Filters Degradation with EMIS-ECIS PWAS" of Giurgiutiu, et al. filed on Jul. 16, 2012, now U.S. Pat. No. 8,814,996; which is (2) a continuation of and claims priority to U.S. patent application Ser. No. 13/309,149 entitled "Methods and Sensors for the Detection of Active Carbon Filters Degradation with EMIS-ECIS PWAS" of Giurgiutiu, et al. filed on Dec. 1, 2011; which (3) claims priority to U.S. Provisional Patent Application, Ser. No. 61/458,735 of Giurgiutiu, et al. entitled "Method and Sensor for the Detection of Active Carbon Filters Degradation with EMIS-ECIS PWAS" filed on Dec. 1, 2010, the disclosures of which are incorporated by reference herein.

GOVERNMENT SUPPORT CLAUSE

This invention was made with government support under W911NF-07-R-003-03 awarded by Army Research Office. The government has certain rights in the invention.

BACKGROUND

Impregnated activated carbon, such as, but not limited to, ASZM-TEDA (Activated Carbon, Impregnated with Copper, Silver, Zinc, Molybdenum, and/or Triethlyenediamine), is used as filter media in individual and collective protection systems used by the military. The high-surface area activated carbon possesses excellent adsorption capacity for physically adsorbing chemical warfare gases. Although the impregnated activated carbon provides excellent initial protection against vapors and acidic/acid-forming gases, the capacity of activated carbon degrades over time from exposure to contaminants, such as $SO_2$ and water condensation. Mechanical integrity defect formation in the carbon filter, such as flow channeling or filter settling, can also impair the filtration performance.

Active carbon filter degradation detection and residual life prediction has been studied by many researchers. Hori et al. used a semiconductor gas sensor to detect breakthrough of organic vapors (Hori et al. 2003); Bernard et al. patented a method using fiber optic chemical sensor for indicating the end of service life of a respirator cartridge (Bernard et al. 2002); Rubel, et al. used electrochemical impedance spectroscopy to detect $SO_2$ and humidity in impregnated active carbon (Rubel et al. 2009).

These methods provide approaches to detect specific chemical presence or sense chemical concentration in the carbon filters. However, current sensing technologies are lacking of the capability of detecting mechanical changes, such as carbon packing, settling flow channeling, etc. Furthermore, the sensors and related measurement device are cumbersome and often has high power requirement, which limited their use in respirator cartridges.

As such, a need exists for methods to detect the degradation of impregnated active carbon filters.

SUMMARY

Objects and advantages of the invention will be set forth in part in the following description, or may be obvious from the description, or may be learned through practice of the invention.

Active carbon filters are generally provided. In one particular embodiment, the active carbon filter can include a carbon filter comprising activated carbon and defining a filter surface; a first piezoelectric wafer active sensor on the filter surface that is electrically isolated from the carbon filter; and a second piezoelectric wafer active sensor on the filter surface that is electrically connected to the filter surface; and an impedance monitoring device electrically connected to the first piezoelectric wafer active sensor and the second piezoelectric wafer active sensor.

Methods are also generally disclosed for determining if any degradation has occurred in an active carbon filter. For example, the method can include monitoring any impedance changes in the first piezoelectric wafer active sensor on the filter surface; and monitoring any impedance changes in the second piezoelectric wafer active sensor on the filter surface.

Systems are also generally disclosed that are operative to detect active carbon filter degradations. The system can include, in one particular embodiment, a plurality of piezoelectric wafer active sensors embedded into an active carbon filtration device; an impedance measurement circuit configured to measure the impedance of each piezoelectric wafer active sensor embedded into the active carbon filtration device; and a signal processor configured to control the impedance measurement circuit to perform impedance measurement on each piezoelectric wafer active sensor embedded into the active carbon filtration device and to process received electromechanical impedance spectroscopy and electrochemical impedance spectroscopy signals from each piezoelectric wafer active sensor embedded into the active carbon filtration device.

Methods are also generally provided for assessing filter degradation status of an activated carbon filter that includes a plurality of piezoelectric wafer active sensors positioned thereon. The method can include, for example, measuring impedance spectra of pristine status at selected frequencies based on the selected methodology; saving pristine spectra data in said signal processor as baseline data; measuring impedance spectra of said piezoelectric wafer active sensors at desired intervals; storing the impedance spectra in the signal processor; and analyzing the measured impedance spectra using selected methodology and compare with the said baseline data to estimate the degradation status of said filter.

Other features and aspects of the present invention are discussed in greater detail below.

BRIEF DESCRIPTION OF THE DRAWINGS

A full and enabling disclosure of the present invention, including the best mode thereof to one skilled in the art, is set forth more particularly in the remainder of the specification, which includes reference to the accompanying figures.

DETAILED DESCRIPTION

Figure 1:
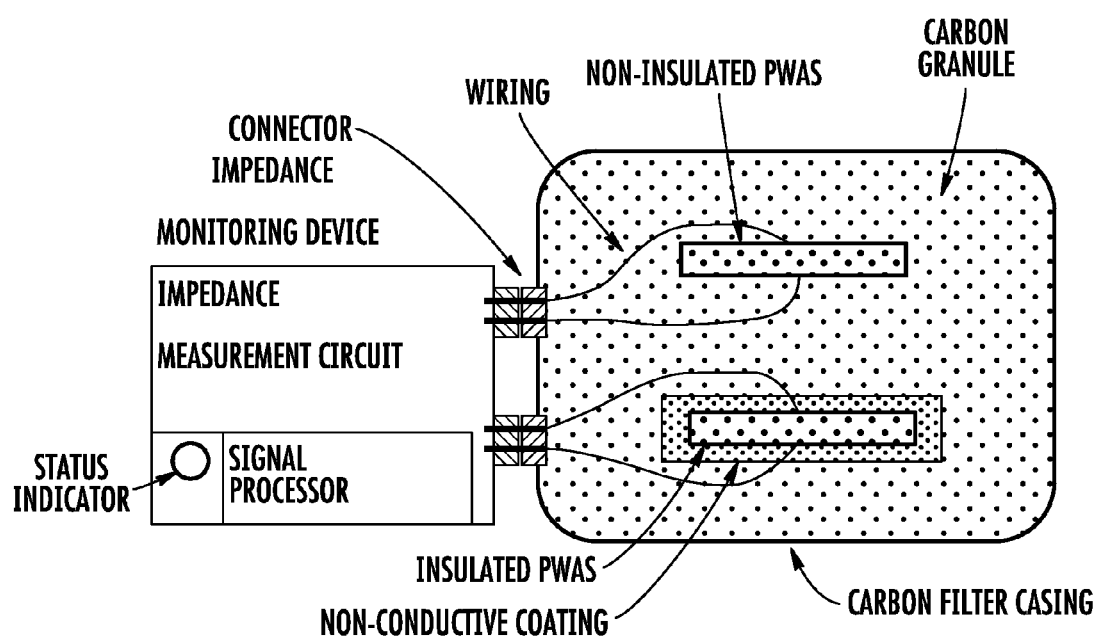
FIG. 1 shows an in-situ degradation detection in active carbon with PWAS.

Reference now will be made to the embodiments of the invention, one or more examples of which are set forth below. Each example is provided by way of an explanation of the invention, not as a limitation of the invention. In fact, it will be apparent to those skilled in the art that various modifications and variations can be made in the invention without departing from the scope or spirit of the invention. For instance, features illustrated or described as one embodiment can be used on another embodiment to yield still a further embodiment. Thus, it is intended that the present invention cover such modifications and variations as come within the scope of the appended claims and their equivalents. It is to be understood by one of ordinary skill in the art that the present discussion is a description of exemplary embodiments only, and is not intended as limiting the broader aspects of the present invention, which broader aspects are embodied exemplary constructions.

In general, the present disclosure is directed to methods and systems for detecting the active carbon filter degradation of piezoelectric wafer active sensors (PWAS), with combined use of electromechanical impedance spectroscopy (EMIS) and electrochemical impedance spectroscopy (ECIS) methods. The combined use of electromechanical impedance spectroscopy (EMIS) and electrochemical impedance spectroscopy (ECIS) with piezoelectric wafer active sensors (PWAS) for degradation detection in active carbon filters can detect electrical and mechanical changes in active carbon filters, which can give a non-intrusive in-situ evaluation method to improve the safety of active carbon filter system. In certain embodiments, the presently disclosed methods can allow for degradation detection in active carbon filters based on the following fundamental objectives: in-situ monitoring, non-obstructive to carbon filter structure, ability to detect both electrical and mechanical changes associated with filter degradation, and/or ability to differentiate electrical and mechanical changes associated with filter degradation.

In one particular embodiment, the presently disclosed method can use embedded PWAS transducers to take EMIS and ECIS measurement and evaluate chemical and mechanical degradations in active carbon filters. Such an approach can allow for the determination of impregnant degradation, water condensation, contamination detection, carbon bed packing, settling and flow channeling, etc., in an active carbon filter. However, the combination of EMIS and ECIS methods can allow for these chemical and mechanical degradations can be differentiated. Degradation detection and characterization is important to identify the cause of such degradation, and provide the filter user early warning for prevention actions. One major potential industrial application for such methods and systems is in active carbon air filtration devices.

The EMIS method measures the coupled high-frequency sensor-structure dynamics in structural health monitoring and biomechanical research (Giurgiutiu 2008, Xu and Giurgiutiu 2006, Giurgiutiu et al. 2004). The ECIS method measures the dielectric properties of the media between two electrodes. When the carbon filter is contaminated (e.g., with chemical agent or water) or integrity defects are formed, its mechanical properties (e.g. density, stiffness, etc.) and electrical properties (conductivity, resistance) will change. The PWAS sensor(s) inside the carbon filter will be able to detect the mechanical changes using EMIS method; and the electrical changes using ECIS method. Because the ECIS and EMIS approaches are different, the combination of these two methods will allow one to differentiate what aspects of filter degradation are monitored better by one method than by the other. PWAS sensor can be configured to sense only mechanical changes, only electrical changes, or to sense both mechanical and electrical changes simultaneously. This approach can also differentiate the changes due to mechanical and electrochemical change.

Thus, in one embodiment, the presently disclosed methods and systems use PWAS as ECIS and EMIS sensors, which can be embedded in the active carbon granules or on the activated carbon filter, to detect electrical and mechanical changes associated with the degradation of active carbon filter.

Piezoelectric wafer active sensors (PWAS) are inexpensive transducers that operate on the piezoelectric principle. PWAS couple the electrical and mechanical effects through piezoelectric effects. PWAS are the enabling technology for active structural health monitoring (SHM) systems. For example, PWAS are described in U.S. Publication No. 2010/0132469 of Giurgiutiu, et al.; U.S. Pat. No. 7,881,881 of Giurgiutiu, et al.; U.S. Publication No. 2009/0188319 of Giurgiutiu, et al.; U.S. Publication No. 2009/0048789 of Yu, et al.; U.S. Publication No. 2008/0288184 of Giurgiutiu, et al.; U.S. Pat. No. 6,996,480 of Giurgiutiu, et al.; and U.S. Pat. No. 7,174,255 of Giurgiutiu, et al., all of which are incorporated by reference herein for the entirety of their disclosures.

The EMIS method measures the dynamic mechanical spectrum of a structure directly with an electric instrument, i.e., an impedance measurement device. Miniaturized impedance measurement approach has been developed in the recent years (Xu and Giurgiutiu 2006), which significantly reduce the complexity, cost and energy requirement for such device, and make impedance spectroscopy devices portable.

The EMIS method has been used extensively in structural health monitoring (SHM) applications (Giurgiutiu, 2008) and biomechanical research (Giurgiutiu et al. 2004). The result of applying the electromechanical impedance method is to generate the dynamic spectrum of the mechanical response of the structure. By observing modifications in the dynamic spectrum, one can infer that mechanical changes have taken place in the investigated structure. The electrochemical impedance spectroscopy measures the electrochemical spectrum of the material and, when the spectrum changes, it infers that changes have taken place at the material level. The EMIS and ECIS method have similarities, in principal because they both measure impedance and both deal with spectral analysis. However, there are several major differences between EMIS and ECIS, as follows:

1. EMIS is a high-frequency method because it measures in the high kHz and MHz frequency range; in contrast, ECIS is a relatively low frequency method because it typically measures in the low kHz range 2. EMIS uses piezoelectric PWAS transducers to couple the electrical and mechanical energies; in contrast, ECIS uses simple electrode probes inserted (or intimately connected to) the material It is apparent that EMIS is a structural-level method whereas ECIS is a material-level method. Therefore, the use of these methods in combination is likely to expand the investigative options by offering multi-scale opportunities (structural scale and material scale). Because the ECIS and EMIS approaches are different, the combination of these two methods will allow one to differentiate what aspects of filter degradation are monitored better by one method than by the other.

In this new approach, PWAS sensors will be used as both EMIS and ECIS sensors. For EMIS measurement, the PWAS will be insulated from the carbon granules with a non-conductive coating. In this configuration, only mechanical changes will be detected. For ECIS measurement, non-insulated PWAS will be used, the measurement will be conducted at low frequency range (several Hz to several kHz range), well below the electromechanical resonance. In this configuration, the two electrodes on the PWAS sensors will be used for ECIS measurement. With measurement data from both ECIS and EMIS methods, one can differentiate the changes due to mechanical and electrochemical change.

FIG. 1 shows a schematic of an exemplary embodiment according to the present invention. Specifically, FIG. 1 shows an in-situ degradation detection in active carbon with PWAS, where the PWAS sizes are exaggerated, and not to scale and can be less than 10 mm in diameter in most embodiments. The PWAS transducer(s) are inserted into or onto the filter during the filter manufacturing process. An impedance monitoring device can be connected to the transducer(s) through connector(s) on the filter. The monitoring device incorporates a impedance measurement circuit and a signal processor. The impedance measurement circuit is configured to measure the ECIS and EMIS spectrum and also to detect the surrounding temperature and humidity for measurement calibration. When the filter is manufactured, a baseline impedance measurement can be taken; with both ECIS and EMIS being stored to non-volatile memory onboard the monitoring device. At desired interval, the monitoring device can measure the ECIS and EMIS spectrum and compare with the baseline impedance data. A damage index can be generated to give a numerical indicator for the severity of the degradation of the active carbon filter. The signal processor is configured to control the measurement activities and perform measurement data evaluations. When the measurement data is available, the signal processor can evaluate the degradation status and use light and sound indicator(s) to inform and warn the filter user.

This method can, in certain embodiments, encompass the following innovative concepts: monitoring active carbon filter degradation with embedded PWAS transducers; use as a QA/QC instrument for determining proper sealing pressure of the gasket of ColPro filters; use of PWAS EMIS to detect mechanical changes associated with active carbon filter degradation; use of PWAS as ECIS sensor, and/or the combined use of EMIS and ECIS method to differentiate mechanical and electrical changes associated with active carbon filter degradation.

The major potential industrial application of the presently disclosed methods and systems is in active carbon air filtration devices. With the inexpensive and non-intrusive PWAS transducers, a simple solution is provided for monitoring active carbon filters for detecting degradations during operation, which can be adopted by industrial and military applications, federal and industrial laboratories, original equipment manufactures, and/or operators of military and related industrials that are required to assure the safety of active carbon filter users.

EXAMPLES

Two groups of tests were conducted to demonstrate the capability of PWAS in detecting electrochemical and mechanical changes in active carbon granules: (a) PWAS for humidity level detection, and (b) PWAS for pressure detection. The test results show that using EMIS-ECIS method, PWAS are able to detect and differentiate electrical and mechanical changes associated with filter degradation, such as water condensation and integrity defect formation; hence can assist carbon filter residual life prediction. The results are presented hereafter.

Figure 2C:
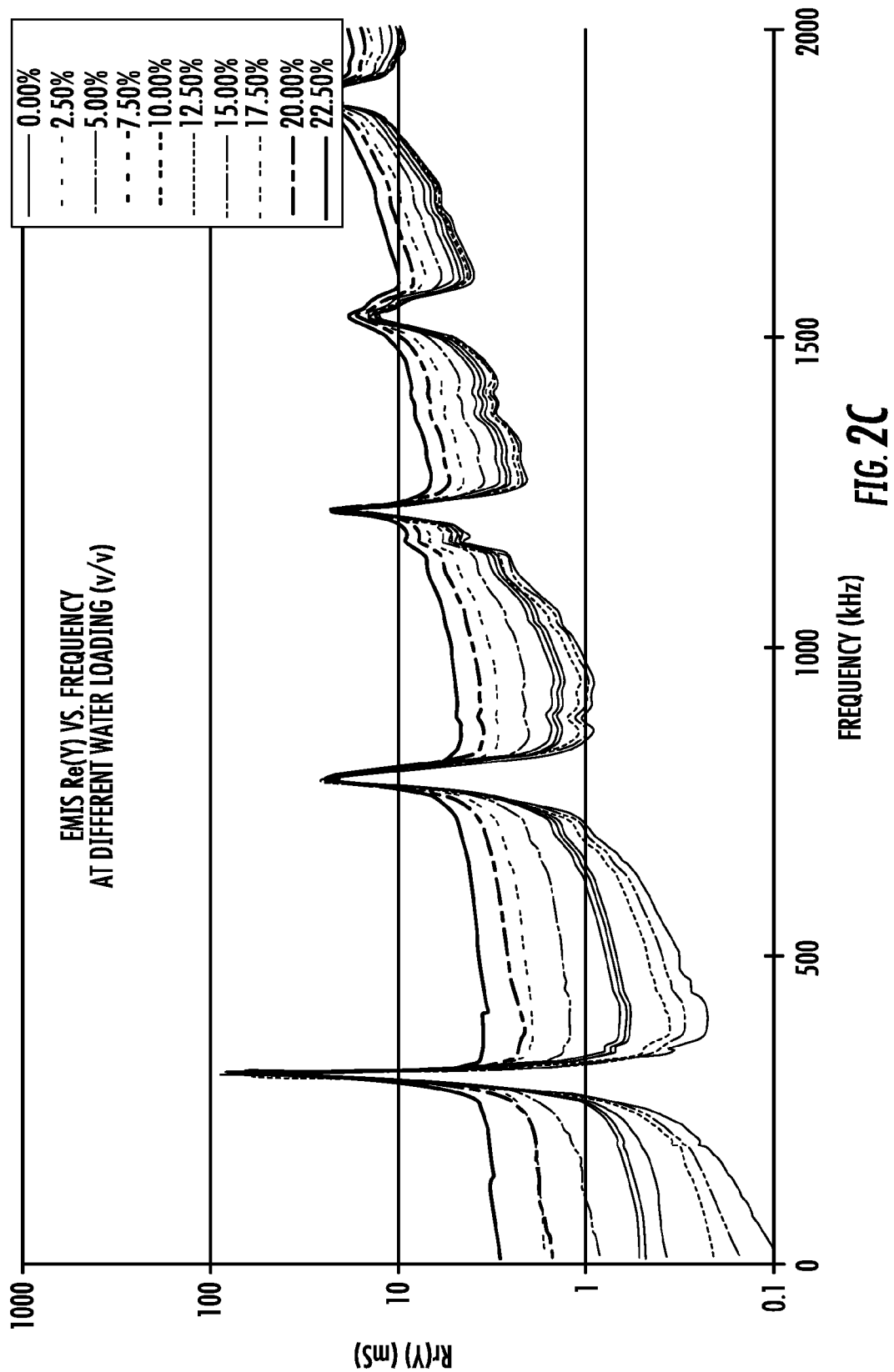
FIG. 2 shows the EMIS vs. frequency: (a) impedance at different humidity (water) levels; (b) impedance at different kerosene levels; (c) admittance at different water levels (d) admittance at different kerosene levels, according to the Examples.
Figure 2D:
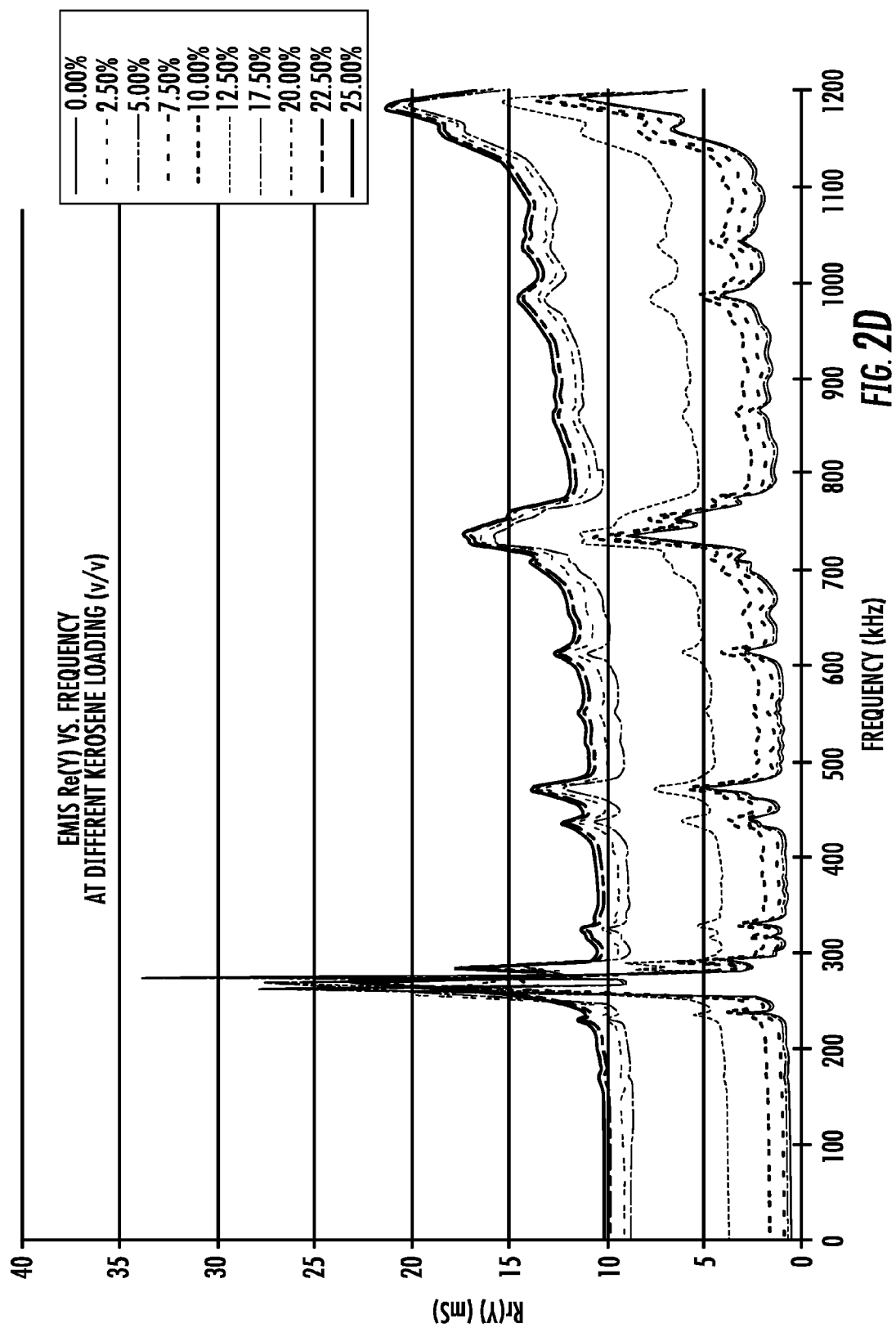

In humidity level detection tests, non-insulated PWAS was embedded into carbon granules, very small amount (2.5% v/v) of water were then incrementally added to the carbon bed; EMIS measurement was taken at each level. FIG. 2 (a) shows the EMIS signals at different water level. Considering the conductivity of water may influence the impedance measurement, we have also tested with kerosene which is non-conductive. Same procedure was taken on kerosene test, and the data are plotted in FIG. 2 (b). To identify the underlying electrical change due to liquid loading level, PWAS admittance was calculated from the impedance data, and plotted in FIGS. 2 (c) and (d). Admittance is the inverse of the impedance. The real part of admittance is the conductance, which measures the conductivity of the material.

For data analysis, three different frequencies were taken to quantify the change pattern in impedance data, shown in FIG. 3 (a). Impedance amplitude at these frequencies was plotted against the water loading level, as shown in FIG. 3 (b). From the plot we have identified that EMIS data kept at low level before it reaches 12.5% water loading level; then EMIS data went up almost linearly with the water loading level.

Figure 3A:
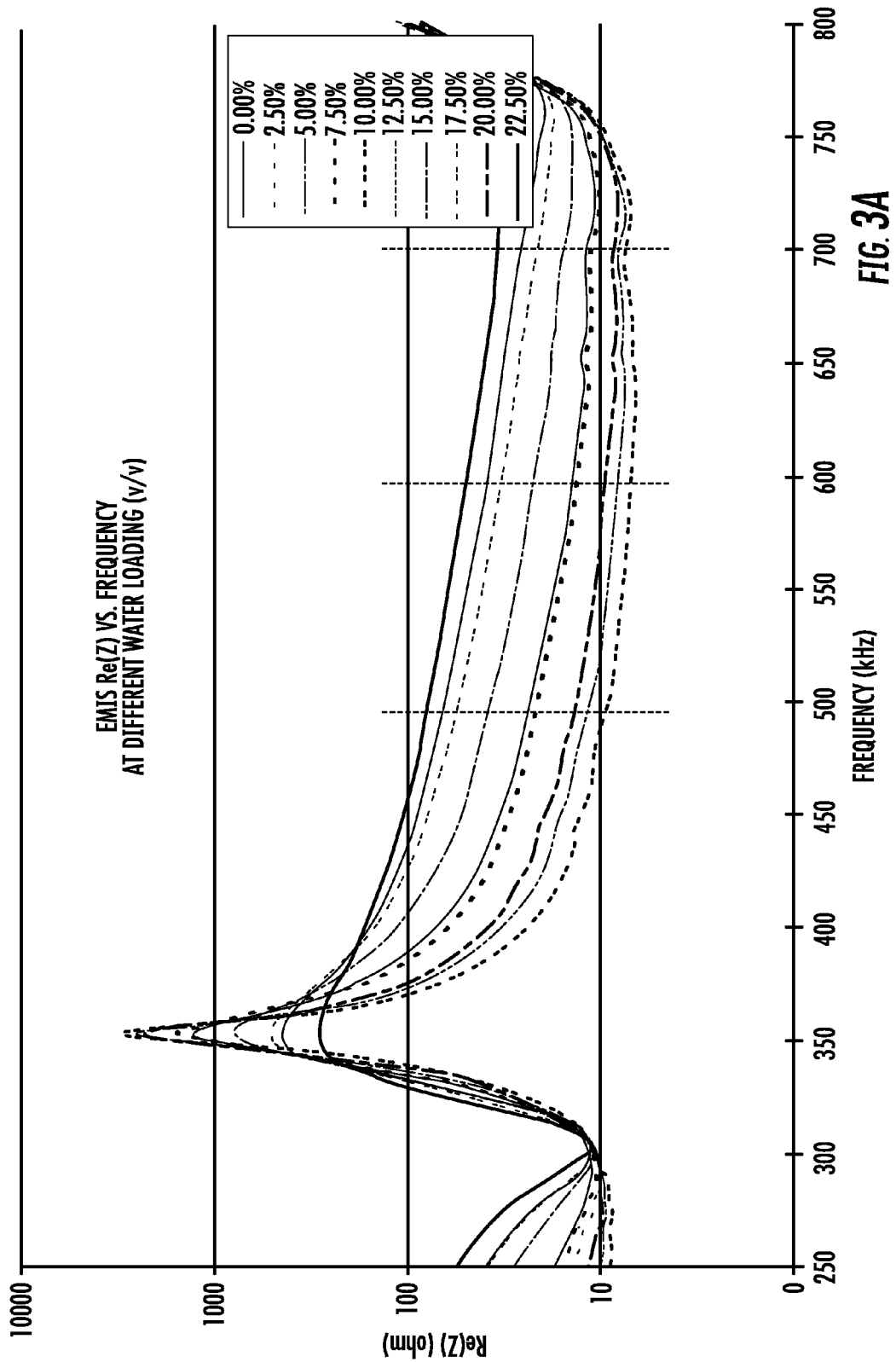
FIG. 3 shows the EMIS signals at selected frequencies show patterns with kerosene and water loading level: (a) water test signals at 500 kHz, 600 kHz, and 700 kHz were selected as indicated by dashed lines; (b) amplitude change in response to water loading level; (c) kerosene test signals at 550 kHz, 600 kHz, and 700 kHz were selected as indicated by dashed lines; (d) amplitude change in respond to kerosene loading level, according to the Examples.
Figure 3B:
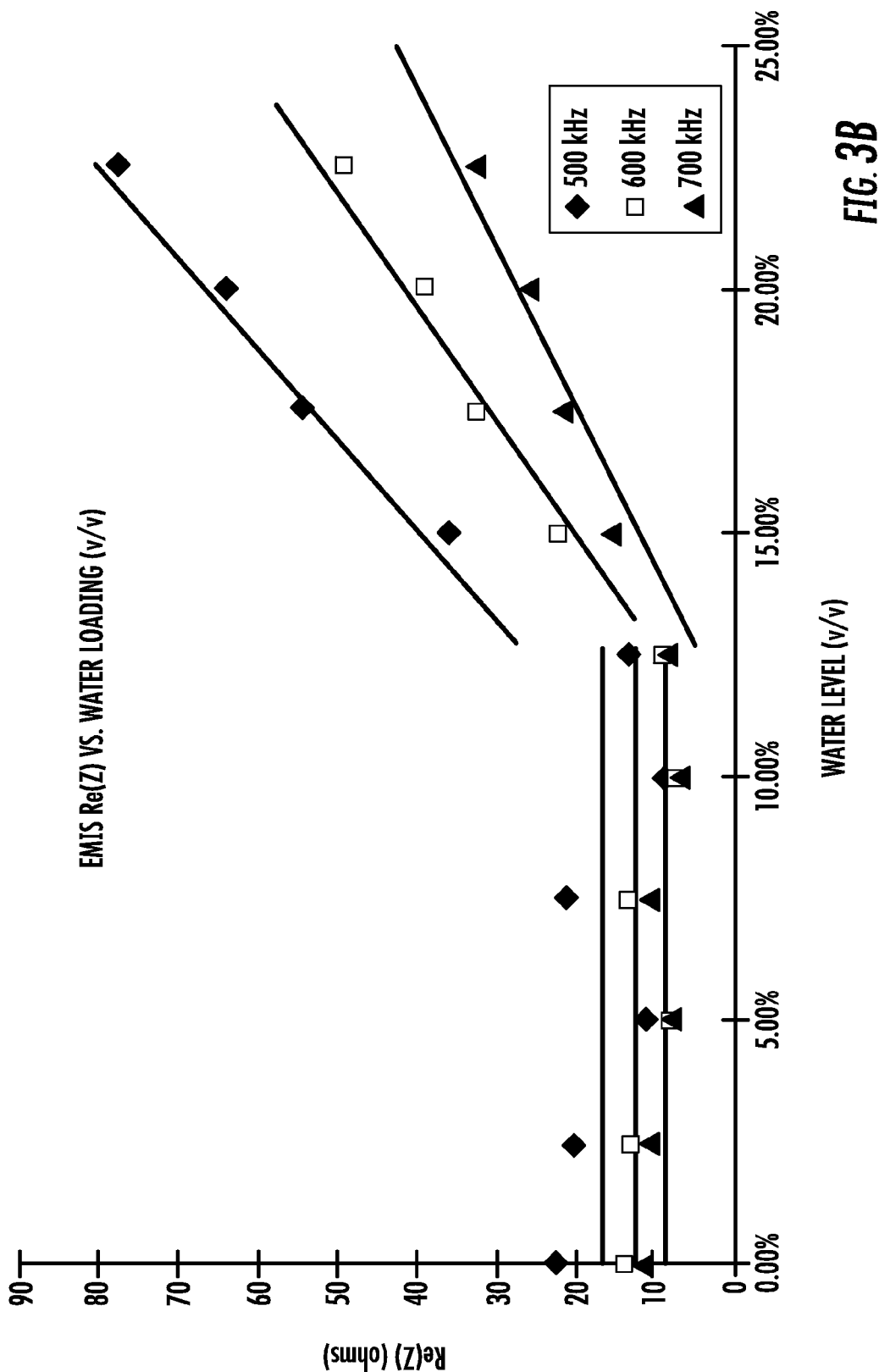
Figure 3C:
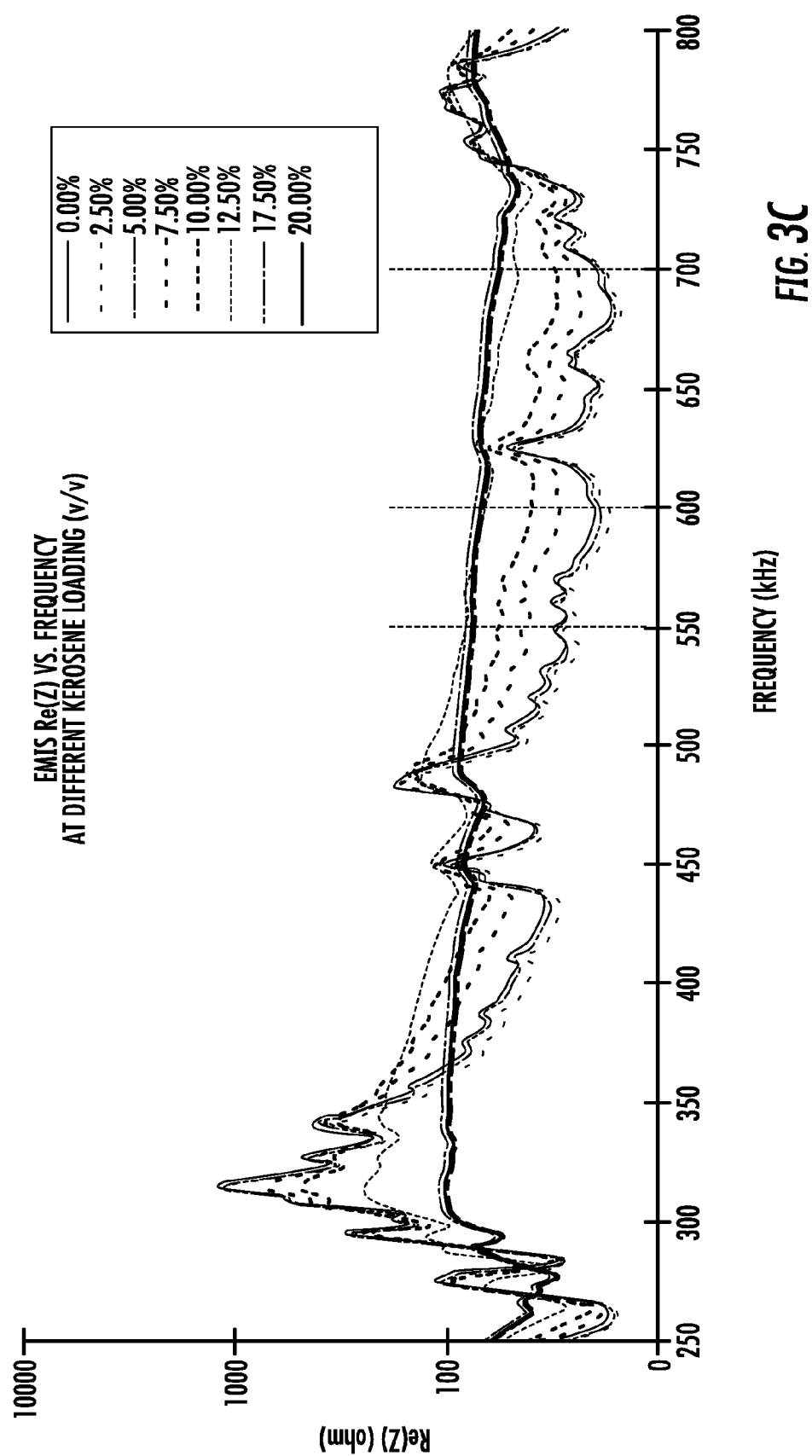
Figure 3D:
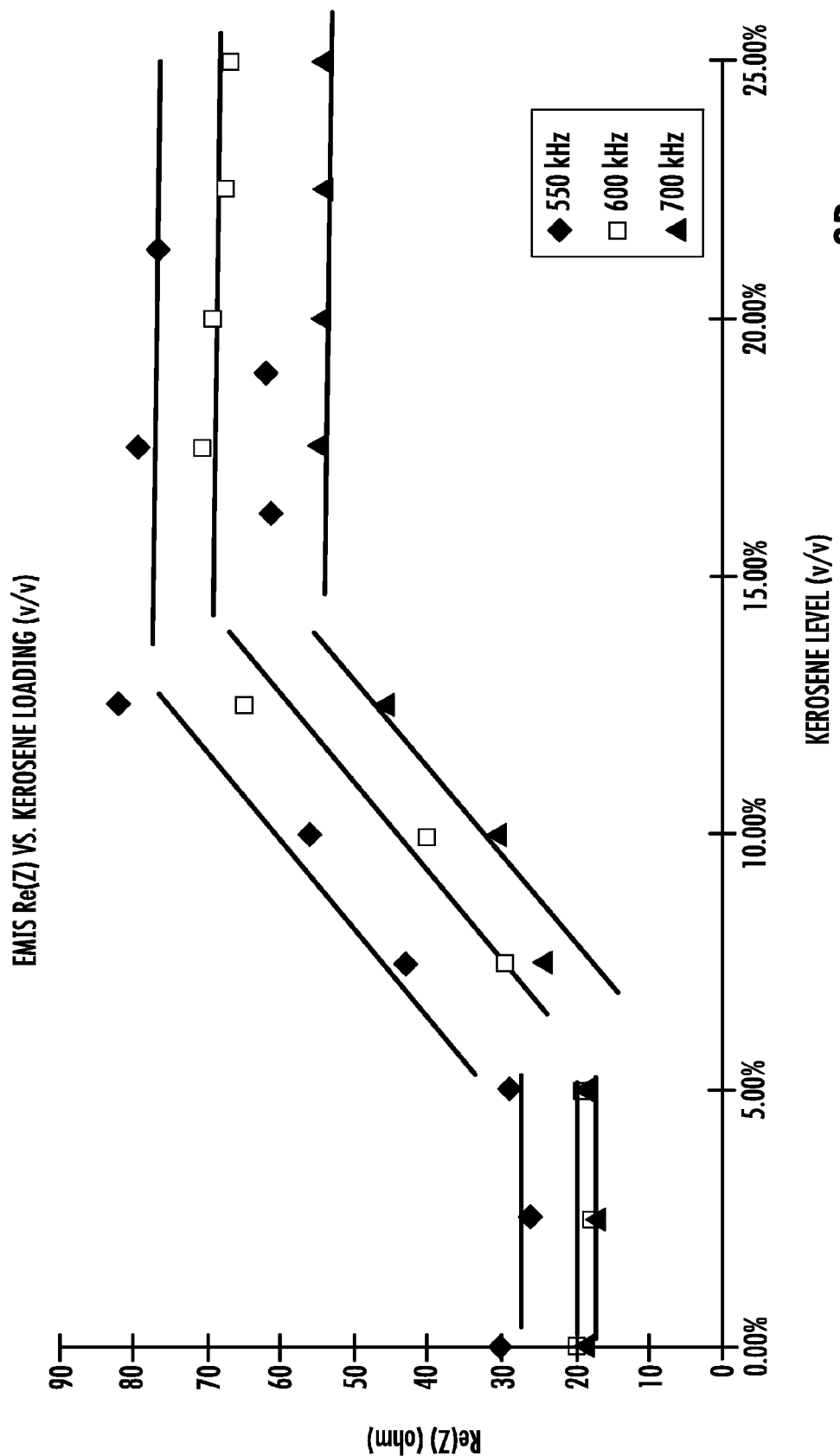
Figure 4A:
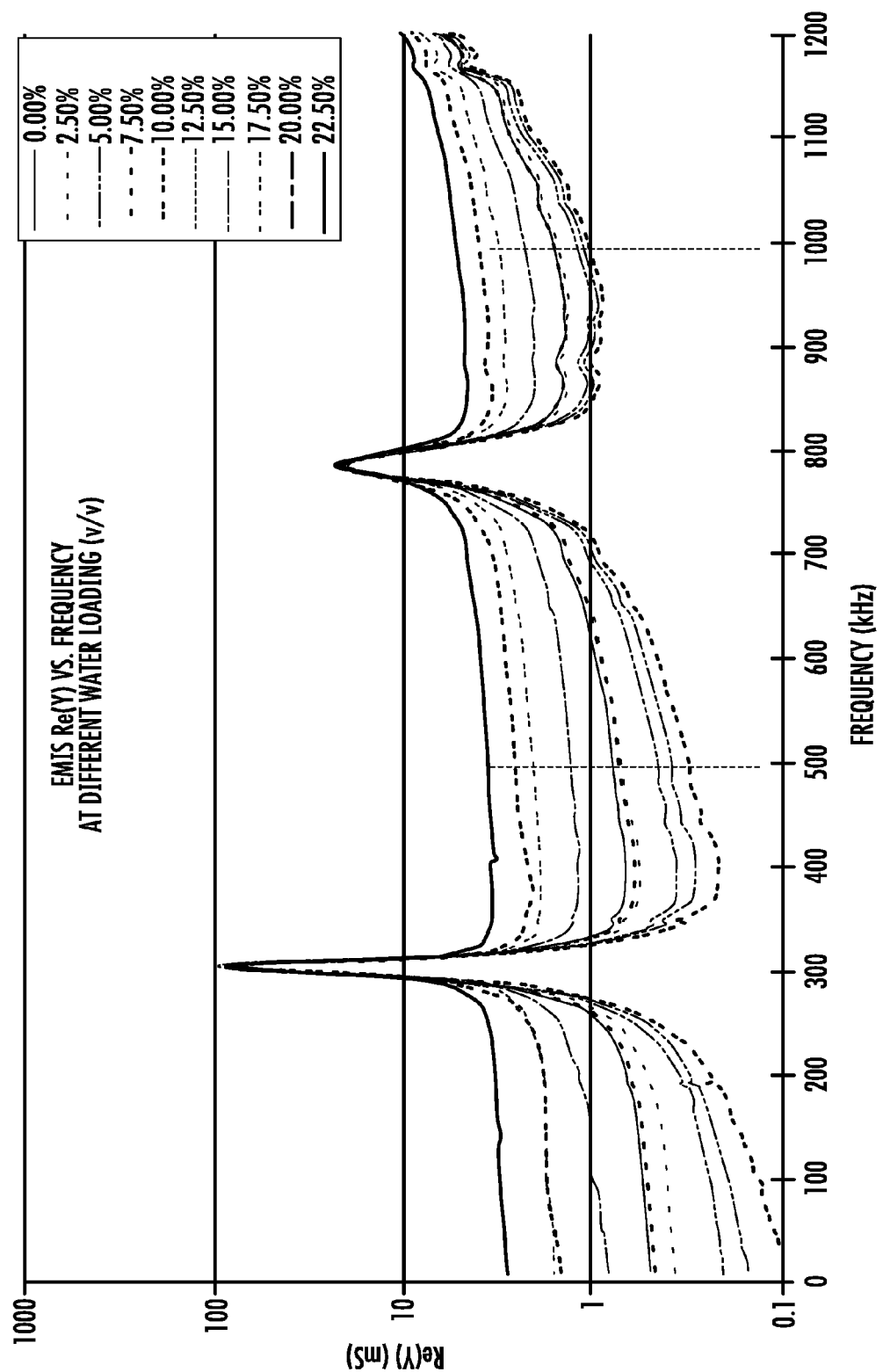
FIG. 4 shows the EMIS admittance at selected frequencies show patterns with kerosene and water loading level: (a) water test data at 500 kHz, and 1000 kHz were selected as indicated by dashed lines; (b) admittance amplitude change in response to water loading levels; (c) kerosene test data at 500 kHz and 1000 kHz were selected as indicated by dashed lines; (d) admittance amplitude change in respond to kerosene loading levels, according to the Examples.
Figure 4B:
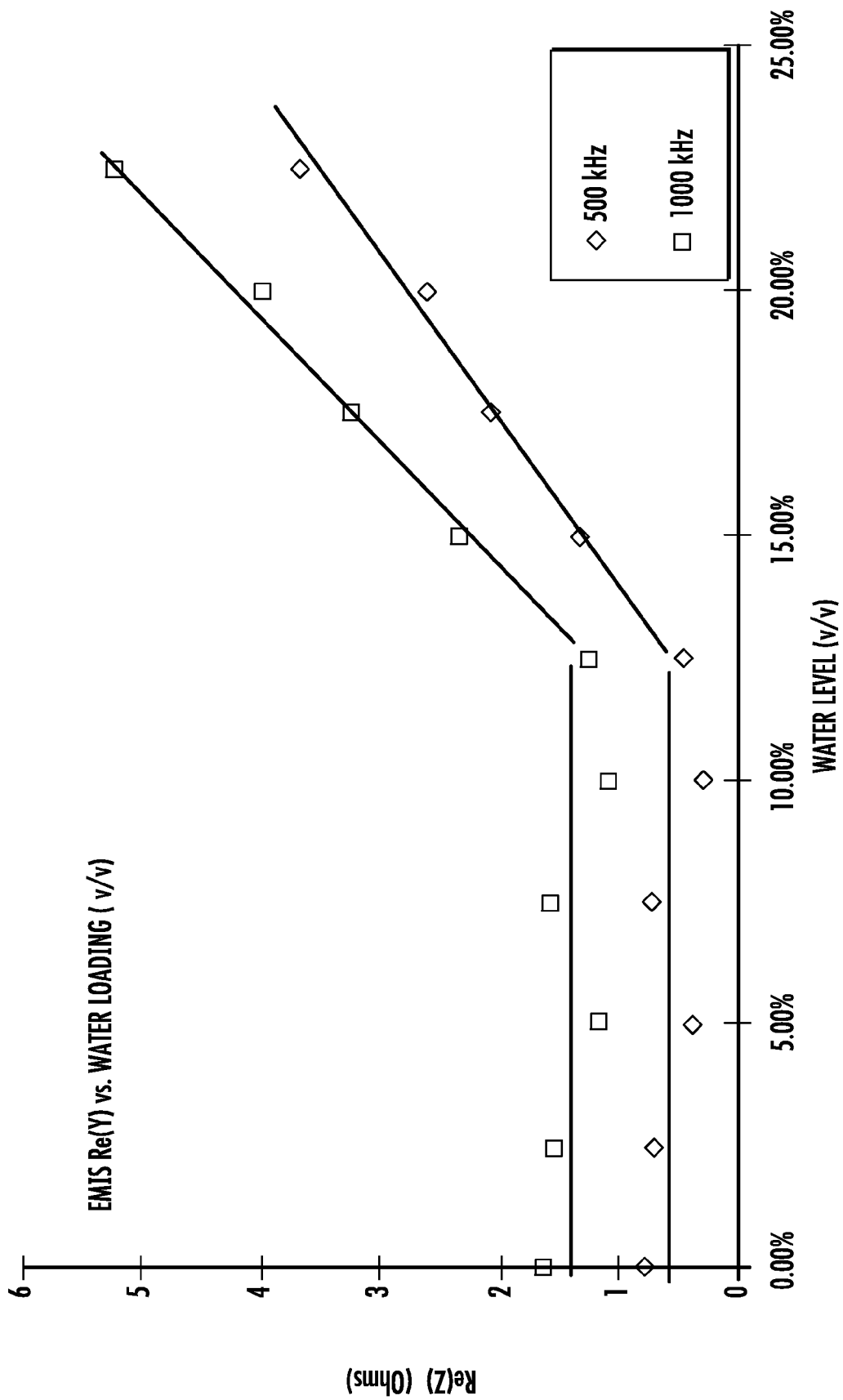
Figure 4C:
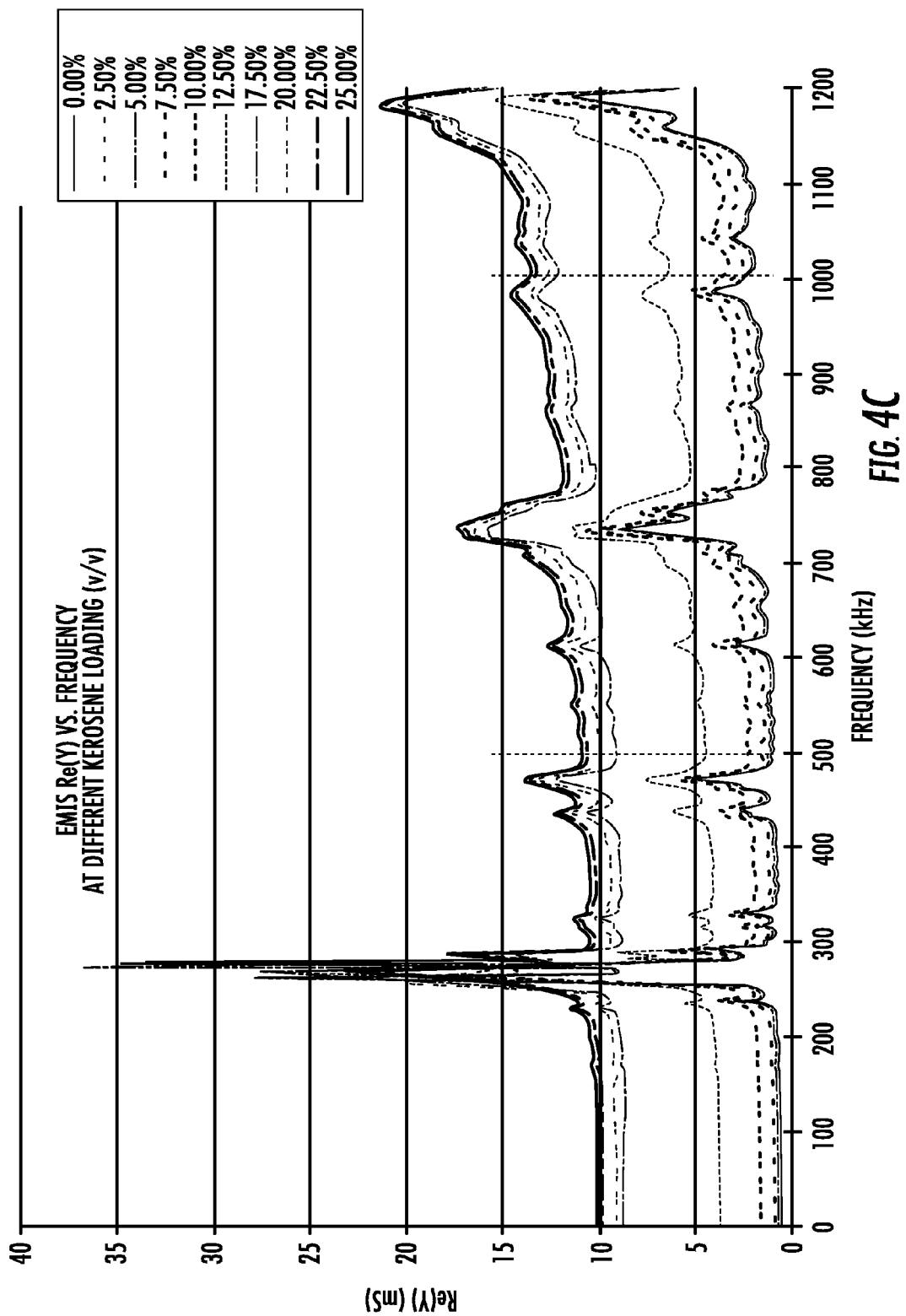
Figure 4D:
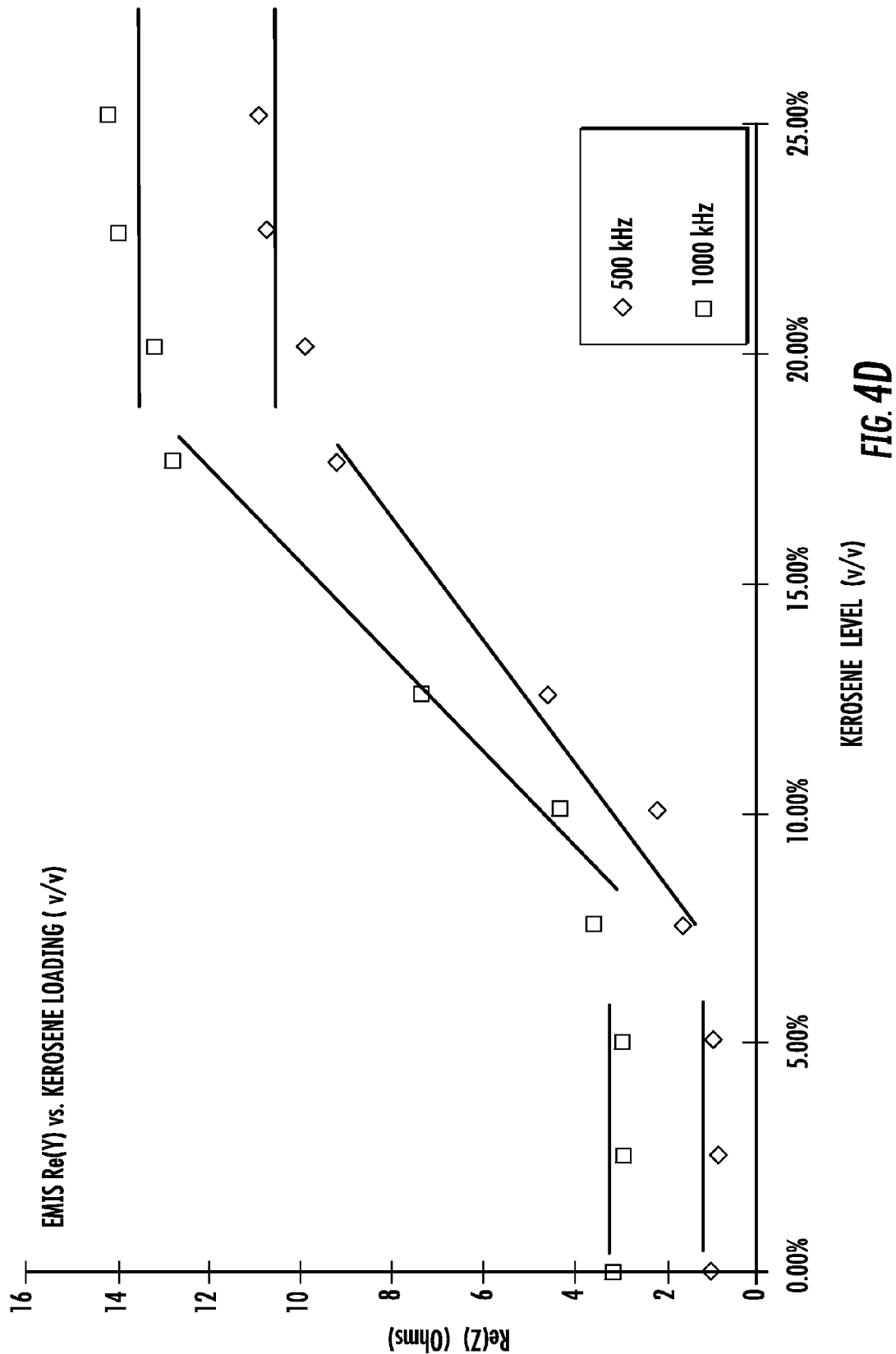

The same approach was taken on the kerosene test data, and the plots are shown in FIGS. 3(c) and (d). It can be seen that with kerosene, the threshold of impedance change changed to 5% volume level, and reaches a plateau at 12.5% volume level.

The admittance data plots show similar pattern. For data analysis, two non-resonances frequencies were selected, and the admittances were compared at different liquid loading levels, as shown in FIG. 4. In water test data plots, FIGS. 4 (a) and (b), the admittance kept at low level at below 12.5% v/v water loading, and then increased almost linearly with the water loading level. In kerosene test data plots, FIGS. 4 (c) and (d), the admittance followed a similar pattern, the admittance was low for kerosene loading level below 5%, and increase almost linearly between 5% and 15%, at kerosene level about 17.5%, the admittance reaches a plateau and increase slowly.

Figure 5A:
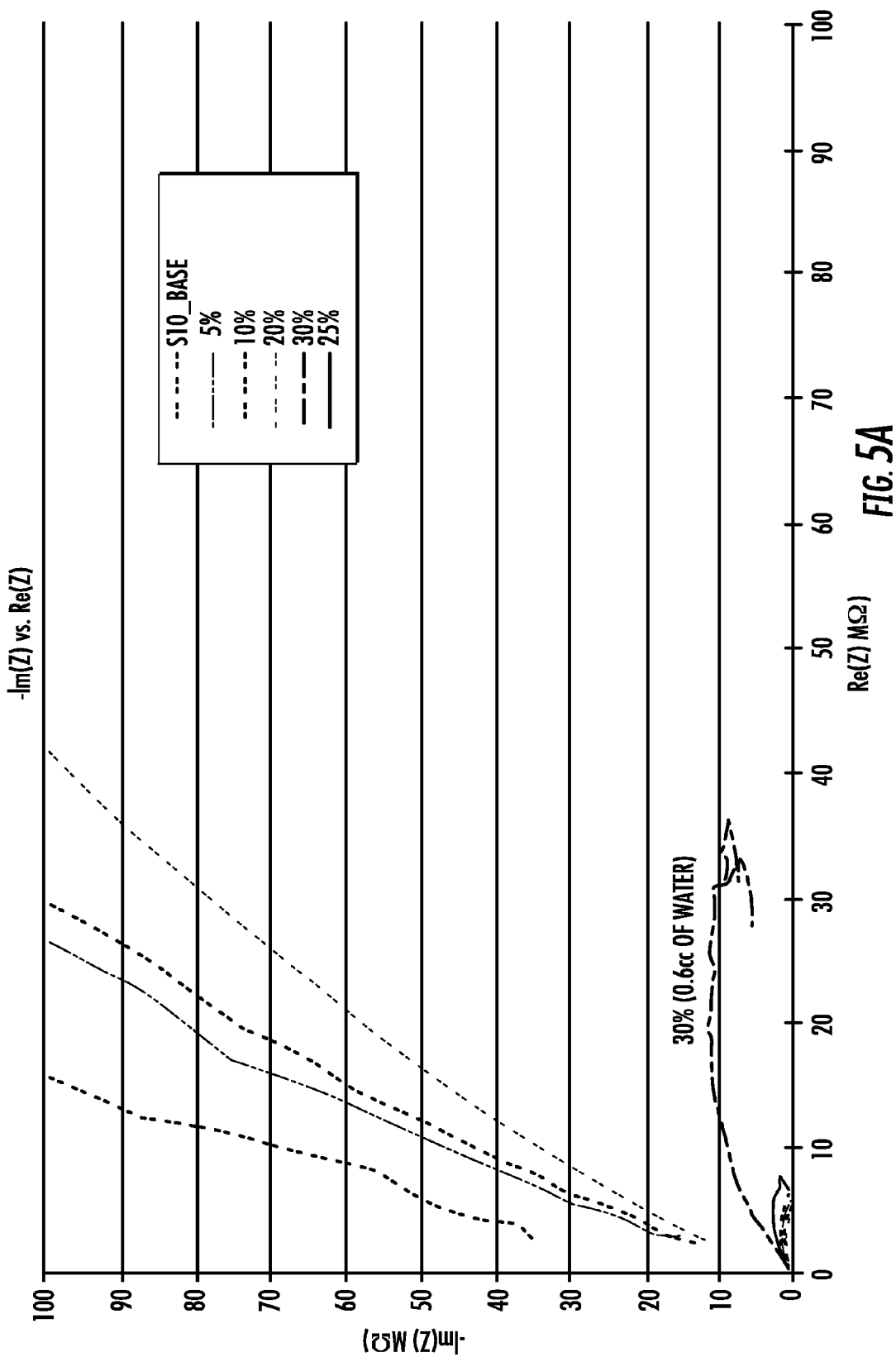
FIG. 5 shows the ECIS data plot for water level test: (a) Nyquist plot, (b) impedance plot, according to the Examples.
Figure 5B:
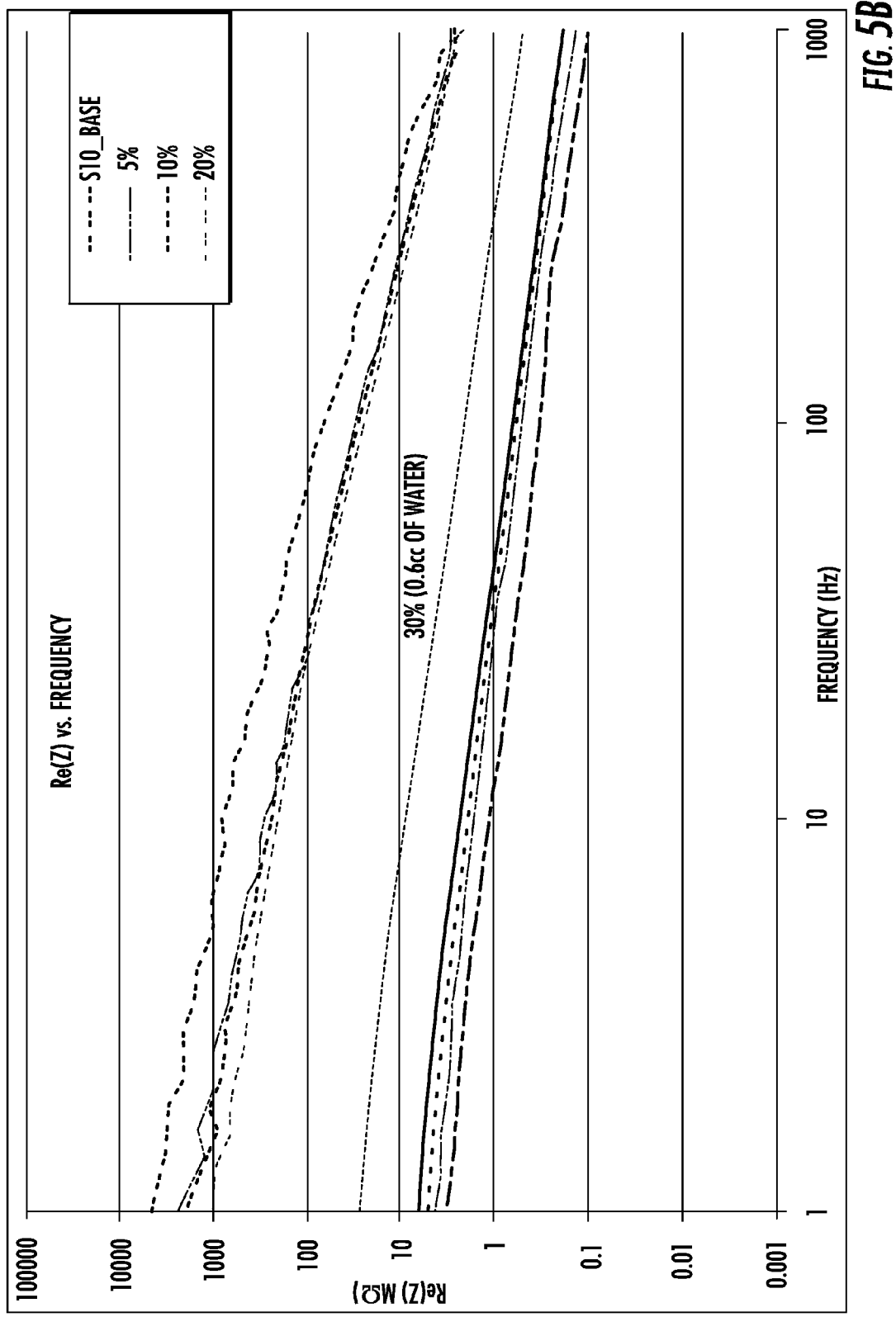

ECIS measurements were also done for the water loading test. As shown in FIG. 5(a), the impedance Nyquist plot shows a pattern of lowering signals with increased water loading. FIG. 5(b) shows the real part of the same group of data plotted against frequency indicating that the impedance decreases with increased water level.

In summary, PWAS embedded in an activated carbon bed can sense the presence of water (or other liquid agent) in the carbon bed. In a certain range the EMIS impedance and admittance change linearly with water level. The threshold and plateau demonstrated PWAS has its sensitivity limit, and saturation levels. These tests demonstrated that PWAS can be used to detect humidity level in the carbon granules through measuring the impedance and admittance.

In the pressure test, increasing pressure was applied to the carbon bed in 0.9 kPa increment steps; EMIS measurements were taken at each step. Some of the experimental data are shown in the Figures. It can be seen that the resonance peaks of impedance curve were reduced greatly when pressure increased. Then, at higher pressure, the peaks went below normal impedance level; seem like "negative" peaks. Finally, at 18 kPa, the non-peak impedance level increased and got flatter, and almost displayed constant level over the observed frequency range.

Figure 7A:
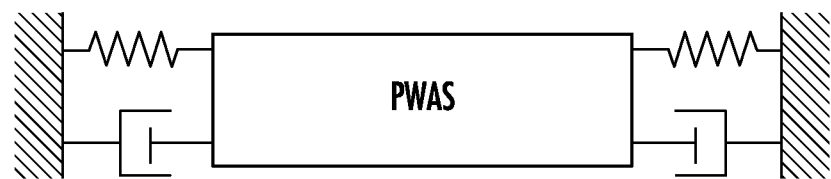
FIG. 7 shows the PWAS-Carbon filter granule model: (a) mechanical model, PWAS is supported by complex spring and damper; (b) electrical model, the PWAS is a capacitor with parallel variable resistor representing the carbon filter granule, according to the Examples.
Figure 7B:
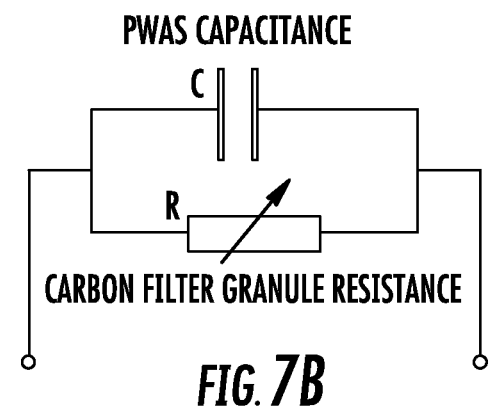
Figure 8A:
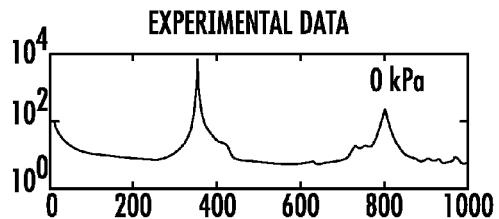
FIG. 8 shows the PWAS-Carbon filter granule model simulation: (a) Impedance data at different pressure levels; and (b) PWAS model simulation with a linear changing factor, according to the Examples.
Figure 8B:
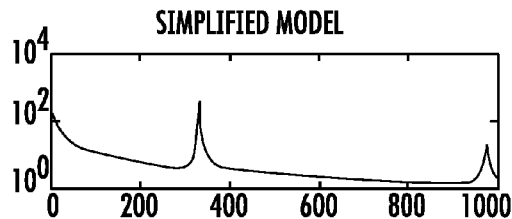
Figure 8C:
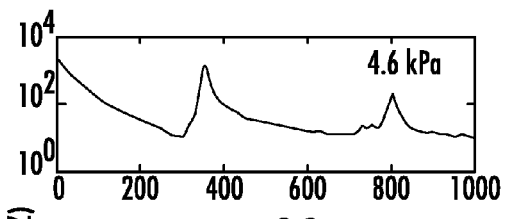
Figure 8D:
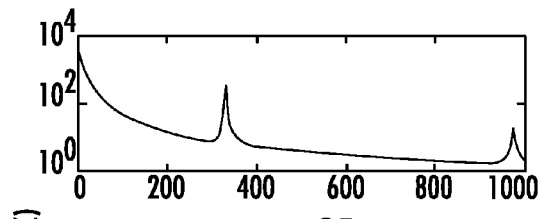
Figure 8E:
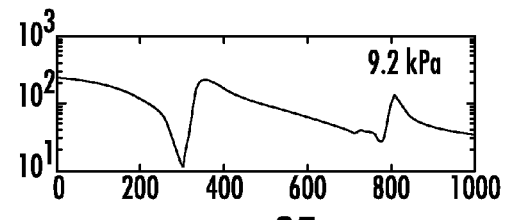
Figure 8F:
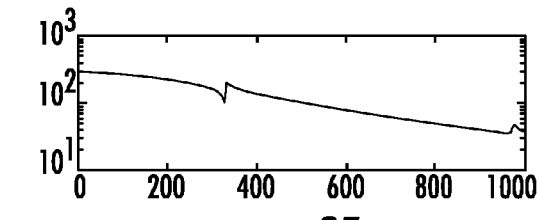
Figure 8G:
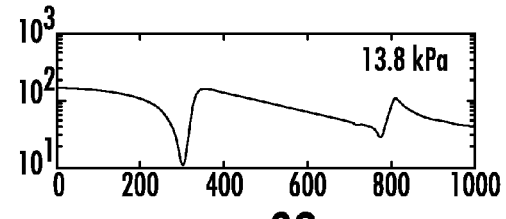
Figure 8H:
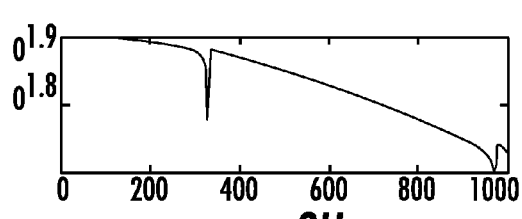
Figure 8I:
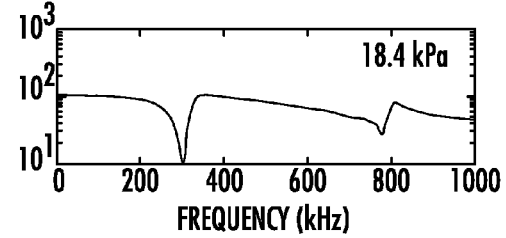
Figure 8J:
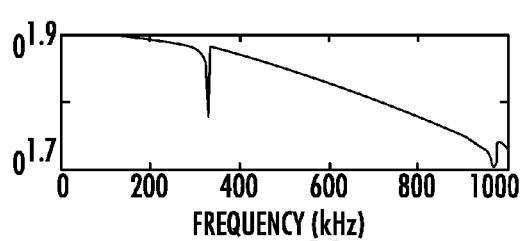

In order to understand these significant changes, a tentative simplified model was created for the PWAS-carbon bed system, as shown in FIG. 7. Mechanically, the carbon bed was considered as a complex spring-damper system supporting the PWAS (FIG. 7a). Electrically, the resistance of carbon granule was modeled as a variable resistor. It was connected in parallel with the PWAS transducer's capacitance. When pressure is increased, the spring-damper becomes stiffer, and carbon resistance decreases. The model was used with increasing pressure levels.

FIG. 8 shows comparison of experimental data and modeling results for increasing pressure levels. Similar pattern of behaviors is observed between experimental data and model.

From experimental data and analytical modeling, we noticed that at high pressure level, the dominant component is the carbon filter granule resistance. When more pressure is applied, the carbon granules contact resistance will decrease. When the pressure goes beyond a certain threshold, the resistance will not increase significantly. Since the PWAS has two conductive electrodes, it can sense not only the mechanical change, but also the electrical (conductivity) changes.

Figure 6:
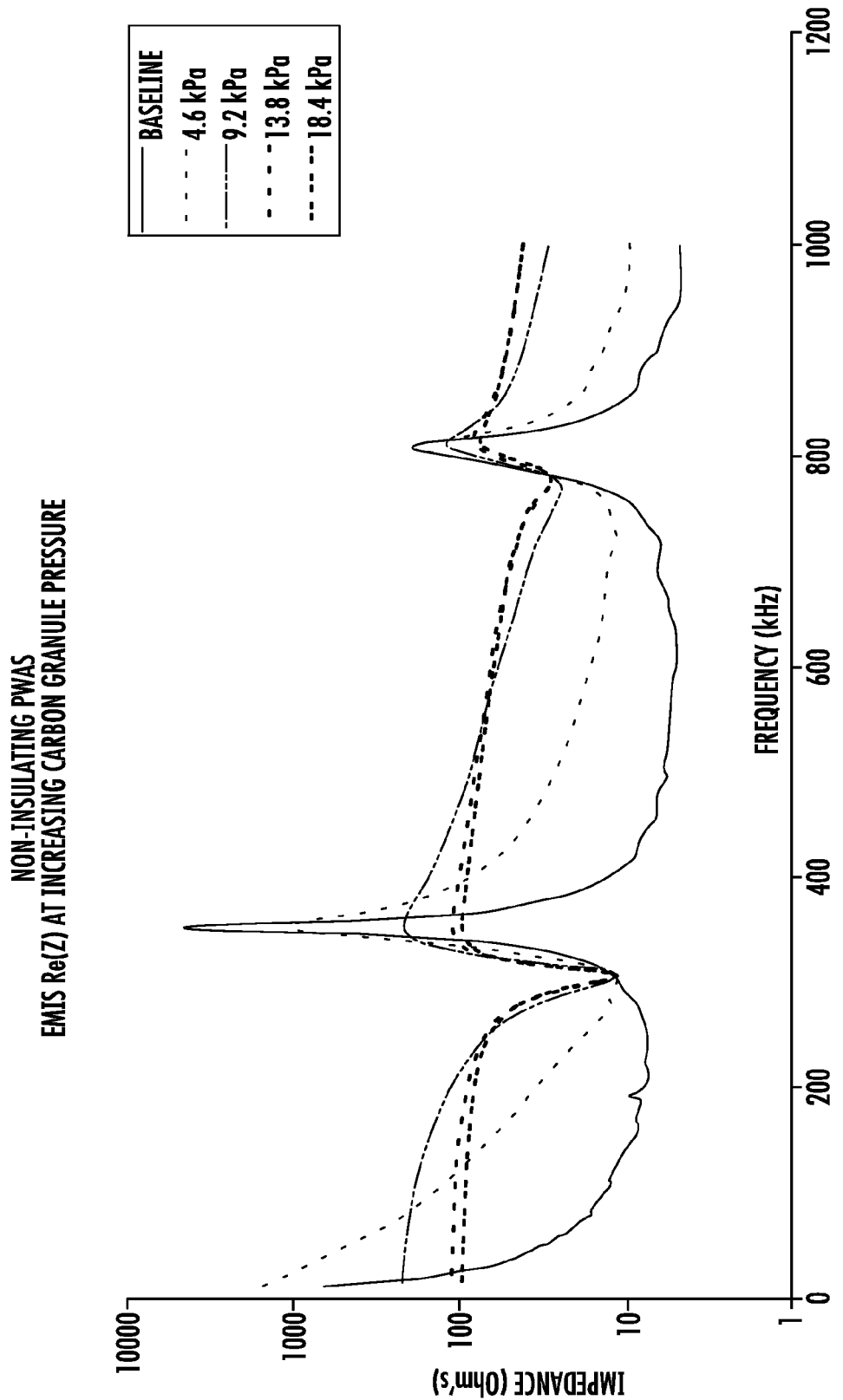
FIG. 6 shows the EMIS impedance from non-insulated PWAS sensors under different pressures, according to the Examples.
Figure 9A:
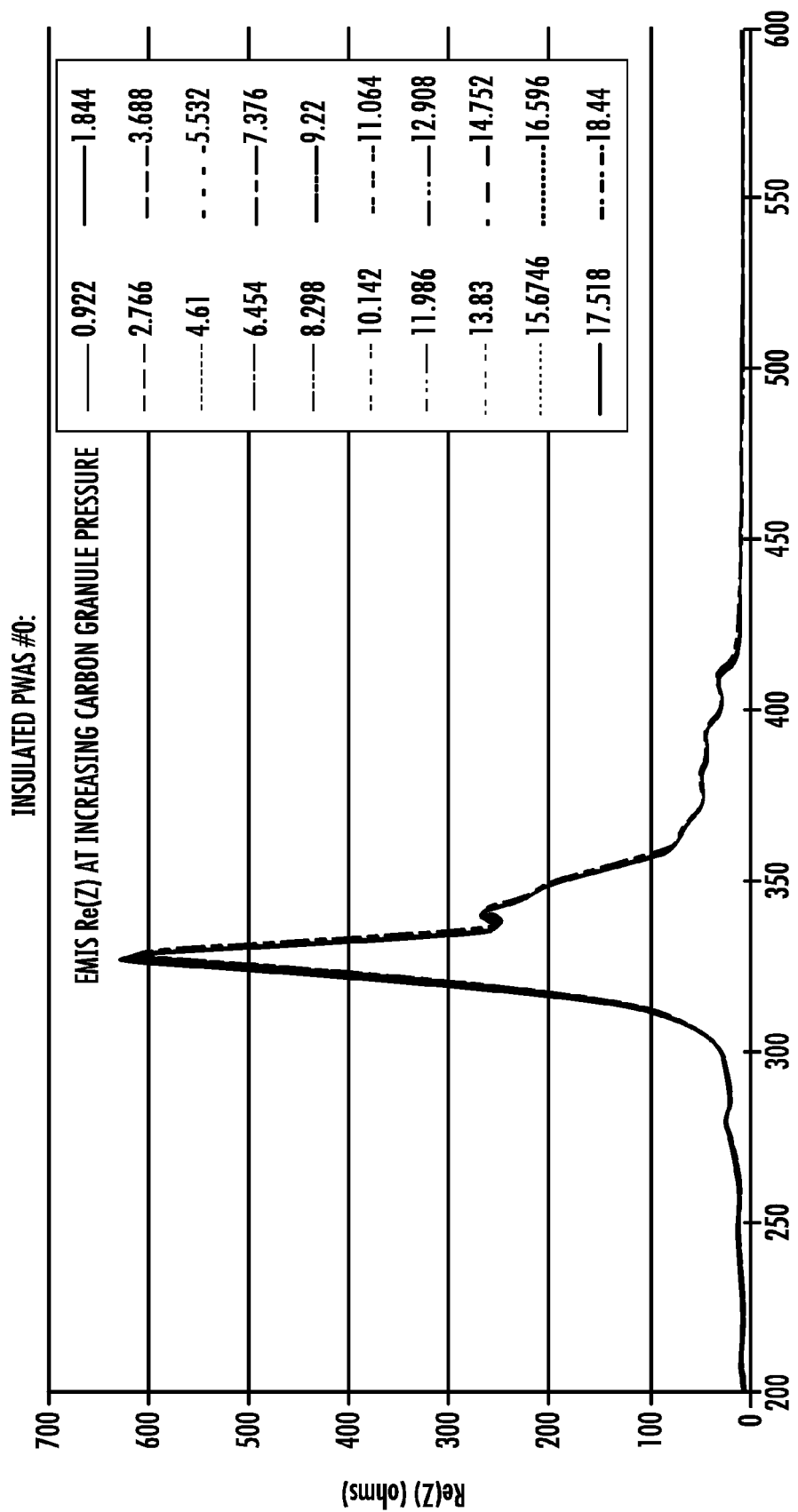
FIG. 9 shows the EMIS impedance of PWAS under different pressure (a) PWAS #0, and (b) PWAS #1, according to the Examples.
Figure 9B:
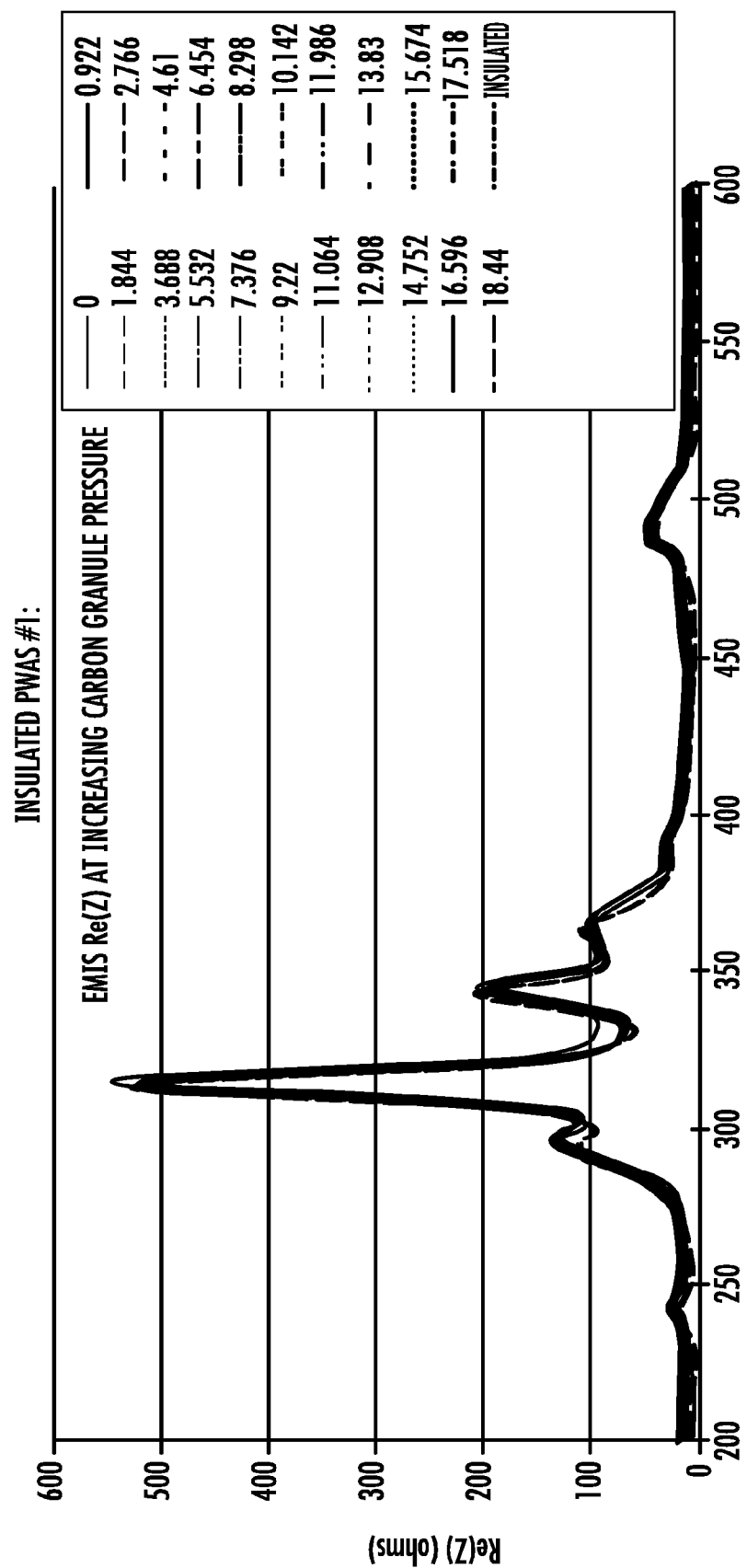
Figure 10A:
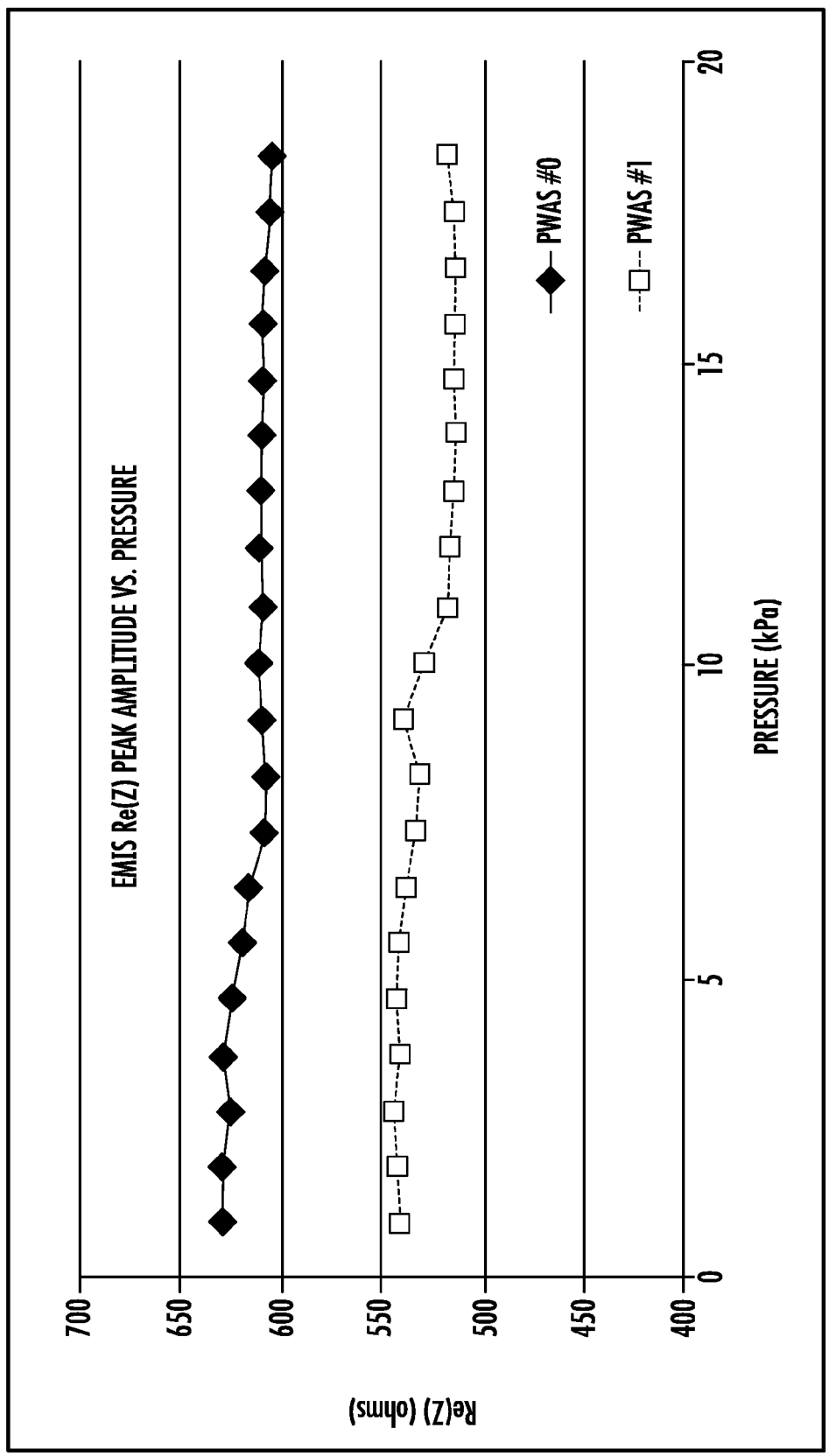
FIG. 10 shows the EMIS impedance peak amplitude and frequency change due to increased pressure, according to the Examples.
Figure 10B:
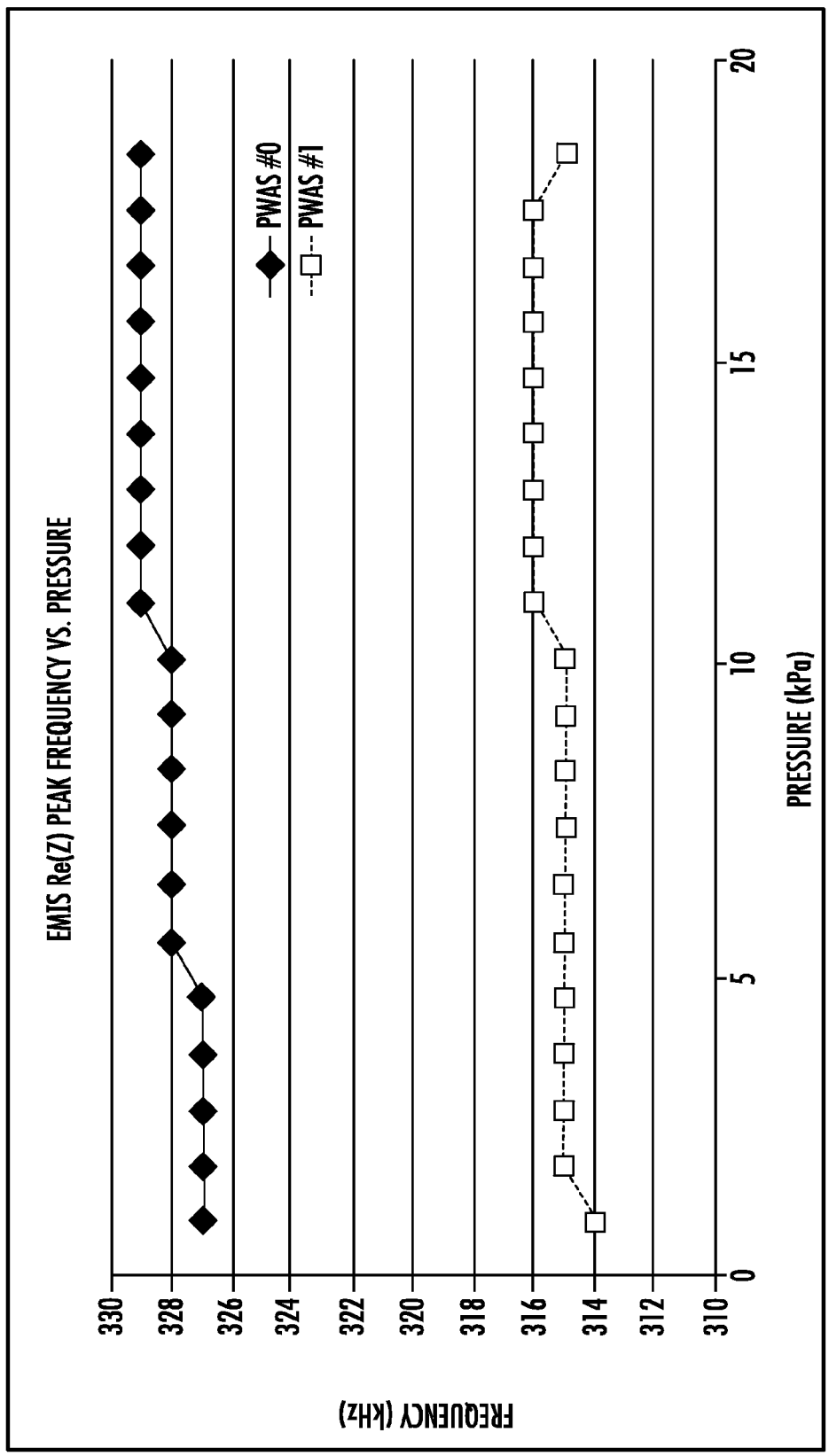

PWAS was also tested as a pure mechanical change detector. Insulated PWAS were manufactured using polyurethane coating and used in a repeated pressure test. The EMIS impedance curves for insulated PWAS are shown in FIG. 9. As different from the bare PWAS (FIG. 6), the insulated PWAS only show minor changes as pressure increased.

However, when the peak amplitude and frequency are plotted against applied pressure, a clear pattern appears, as shown in the Figures. The peak amplitude decreases and frequency increases with added pressure. This matches our previous knowledge about PWAS behavior when the support stiffness changes.

These and other modifications and variations to the present invention may be practiced by those of ordinary skill in the art, without departing from the spirit and scope of the present invention, which is more particularly set forth in the appended claims. In addition, it should be understood the aspects of the various embodiments may be interchanged both in whole or in part. Furthermore, those of ordinary skill in the art will appreciate that the foregoing description is by way of example only, and is not intended to limit the invention so further described in the appended claims.

REFERENCES

[1] Giurgiutiu, V. (2008) Structural Health Monitoring with Piezoelectric Wafer Active Sensors, Elsevier Academic Press, 760 pages, ISBN 978-0120887606, 2008
[2] Xu, B. and Giurgiutiu, V. (2006) "Development of DSP-based Electromechanical (E/M) ImpedanceAnalyzer for Active Structural Health Monitoring", In SPIE's 13th International Symposium on Smart Structures and Materials and 11th International Symposium onNDE for Health Monitoring and Diagnostics, Health Monitoring and Smart NDE of Structural and BiologicalSystems Conference, eds. M. Tomizuka, C.-B. Yun & V. Giurgiutiu. San Diego, Calif. USA, 2006
[3] Giurgiutiu, V., Friedman, H., Bender, J., Borg, T., Yost, M. J., Newcomb, W., et al. (2004). "Electromechanical impedance sensor for in vivo monitoring the body reaction to implants" Journal of Investigative Surgery, 17, 257-270. doi: 10.1080/08941930490502835
[4] Rubel, G. O., Peterson, G. W., Fletcher, N. K., Parker, J. E. & Jeffers, R. B. (2009) "Measurement of the impedance change of impregnated activated carbon during exposure to SO2 vapors at ambient temperatures", Carbon, 47, 3566-3573, 2009
[5] Hori, H., Ishidao, T., and Ishimatsu, S. (2003) Development of a new respirator for organic vapors with a breakthrough detector using a semiconductor gas sensor. Applied Occupational and Environmental Hygiene, 18, 90-95.
[6] Bernard, P., Caron, S., St. Pierre, M., and Lara, J. (2002) End-of-service indicator including porous waveguide for respirator cartridge, Institut National D'Optique, Quebec, U.S. Pat. No. 6,375,725
[7] Fazzino, P. D.; Reifsnider, K. L.; Majumdar, P. (2009) "Impedance spectroscopy for progressive damage analysis in woven composites", Composites Science and Technology, 69 (11-12), 2008-2014. doi: 10.1016/j.compscitech.2009.05.007
[8] Giurgiutiu, V., (2006) "In-Situ Structural Health Monitoring, Diagnostics and Prognostics System Utilizing Thin Piezoelectric Sensors" U.S. Pat. No. 7,024,315 B2, Date of Patent Apr. 4, 2006

What is claimed:
1. A method of assessing filter degradation status of an activated carbon filter, wherein a plurality of piezoelectric wafer active sensors are positioned on the activated carbon filter, the method comprising:
    measuring impedance spectra of pristine status at selected frequencies based on a selected methodology;
    saving pristine spectra data in said signal processor as baseline data;
    measuring impedance spectra of said piezoelectric wafer active sensors at desired intervals;
    storing the impedance spectra in the signal processor; and
    analyzing the measured impedance spectra using the selected methodology and compare with the said baseline data to estimate the degradation status of said filter, wherein the active carbon filter comprises a carbon filter comprising activated carbon and defining a filter surface, and wherein the plurality of piezoelectric wafer active sensors comprise:

a first piezoelectric wafer active sensor on the filter surface, wherein the first piezoelectric wafer active sensor is electrically isolated from the carbon filter;

a second piezoelectric wafer active sensor on the filter surface, wherein the second piezoelectric wafer active sensor is electrically connected to the filter surface.

2. The method of claim 1, wherein the impedance spectra of the piezoelectric wafer active sensors are measured by an impedance monitoring device electrically connected to the first piezoelectric wafer active sensor and the second piezoelectric wafer active sensor.

3. The method of claim 1, wherein an insulating layer is positioned between the filter surface and the first piezoelectric wafer active sensor to electrically isolate the first piezoelectric wafer active sensor from the carbon filter.

4. The method of claim 1, wherein the second piezoelectric wafer active sensor is directly on the filter surface.

5. The method of claim 1, further comprising:
determining if any degradation of the active carbon filter has occurred.

6. The method of claim 5, wherein determining if any degradation of the active carbon filter has occurred, comprises:

monitoring any impedance changes in the first piezoelectric wafer active sensor on the filter surface; and monitoring any impedance changes in the second piezoelectric wafer active sensor on the filter surface.

\* \* \* \* \*